United States Patent [19]

Morgan

[11] 4,203,199

[45] May 20, 1980

[54] SOLID STATE SENSOR

[75] Inventor: Michael J. Morgan, Syracuse, N.Y.

[73] Assignee: Inficon Leybold-Heraeus, Inc., East Syracuse, N.Y.

[21] Appl. No.: 947,824

[22] Filed: Oct. 2, 1978

Related U.S. Application Data

[62] Division of Ser. No. 841,285, Oct. 12, 1977, Pat. No. 4,171,341.

[51] Int. Cl.$^2$ .............................................. H01C 7/02
[52] U.S. Cl. ....................................... 29/612; 29/613; 29/614; 73/27 R
[58] Field of Search ................ 73/23, 27 R; 29/25.13, 29/610, 612, 613, 611, 614; 324/33; 313/7

[56] References Cited

U.S. PATENT DOCUMENTS

| 2,873,342 | 2/1959 | Drugmand | 29/614 |
| 3,439,262 | 4/1969 | Roberts | 313/7 X |
| 3,471,746 | 10/1969 | Roberts | 324/33 X |
| 3,751,968 | 8/1973 | Loh | 73/27 R X |
| 3,979,625 | 9/1976 | Roberts | 73/27 R X |
| 4,011,654 | 3/1977 | Beaudoin | 29/612 |

*Primary Examiner*—William R. Briggs
*Attorney, Agent, or Firm*—Bruns & Jenney

[57] ABSTRACT

A method of manufacturing a solid state sensor wherein a reactive compound of an alkali metal is tightly packed between a central electrode and a surrounding ion shield. A heating coil is wound about the outside of the shield. The ion shield is formed of a material that is deplete in ions of alkali metal and serves as a ion depletion boundry in the system.

6 Claims, 2 Drawing Figures

SOLID STATE SENSOR

BACKGROUND OF THE INVENTION

This is a division of application Ser. No. 841,285 filed Oct. 12, 1977, now U.S. Pat. No. 4,171,341.

This invention relates to an improved solid state sensing device for selectively detecting the presence of a given constituent within an atmosphere.

A solid state sensor having the ability of detecting the presence of many undesirable gases and vapors within an atmosphere is disclosed by Loh in U.S. Pat. No. 3,751,968. A solid state element, that contains alkali metal ions which readily accept negative ions of the subject gases and vapors, is specially prepared to create an outer layer along its boundaries that is deplete of ions. The conductivity of the element at ambient conditions is negligible. Heating the element, however, in the presence of one or more of the reactive gases and vapors causes ions to flow across the depletion boundary and increase the conductivity of the element. Electrical circuit means are provided for detecting an increase in the conductivity of the element and generating a signal indicative of the presence of a reactive constituent in the test atmosphere.

The Loh type device has proven to be an extremely useful tool for sensing the presence or absence of a halogen gas within a specific atmosphere. Special applications include leak detection in refrigeration equipment and the presence of potentially dangerous gases within an operating room or the like. However, many test atmospheres contain more than one constituent that can react with the sensing element and, as a result, unwanted interference signals are sometimes generated that make it difficult to discern the presence of a single gas or vapor of immediate interest. Water vapor, which is ordinarily present in air, has the ability to trigger the sensor and has proven to be troublesome when air sampling is required. Because most prior art sensors of this type lack discrimination, it heretofore has been the practice in many applications to isolate the sensing element and pretreat the atmosphere prior to sampling in order to avoid erroneous triggering of the device. This, of course, increases the complexity and cost of the equipment and seriously limits its applicability.

It should be further noted that fabrication of the Loh sensor involves the building up of the solid state element around a central electrode contained within an electrical heating element. Because of the size of the components involved and the nature of the materials employed, this has proven to be a tedious and time consuming task requiring mostly hand labor. As a consequence, the volume rate of unit production is relatively low and the cost per unit relatively high.

SUMMARY OF THE INVENTION

It is therefore an object of the present invention to improve solid state sensing devices of the type employing a reactive material containing alkali metal ions capable of accepting the negative ion of many known constituents brought into reactive contact therewith.

A further object of the present invention is to provide a solid state sensing device capable of selectively sensing the presence of one reactive constituent in an atmosphere containing other reactive constituents.

Another object of the present invention is to simplify the method of fabricating a solid state sensing element for detecting the presence of a given gas or vapor within an atmosphere.

Yet another object of the present invention is to provide a solid state sensing device for selectively detecting the presence of a halogen gas within an atmosphere containing water vapor.

These and other objects of the present invention are attained by means of a sampling apparatus including a solid state sensing element formed of a reactive material containing alkali metal ions, a shield enclosing the element that is formed of a material that is substantially devoid of metal ions and which functions as a control screen to selectively pass ions of a given gas or vapor into reactive contact with the solid state element when heated, in the presence of the given gas or vapor, to a predetermined temperature, a heating element positioned about the outer surface of the shield and electrical means operatively associated with the apparatus for detecting a flow of ions through said shield and generating a perceptive signal in response thereto.

BRIEF DESCRIPTIONS OF THE DRAWINGS

For a better understanding of the present invention as well as other objects and further features thereof, reference is had to the following detailed description of the invention to be read in connection with the accompanying drawings, wherein:

FIG. 1 is an enlarged plan view in section showing an improved solid state sensor housed within a hand held instrument which embodies the teachings of the present invention; and FIG. 2 is a simplified schematic representation of the sensor illustrated in FIG. 1 more clearly defining the operation thereof.

DESCRIPTION OF THE PREFERRED EMBODIMENT

Figures 1, 2:
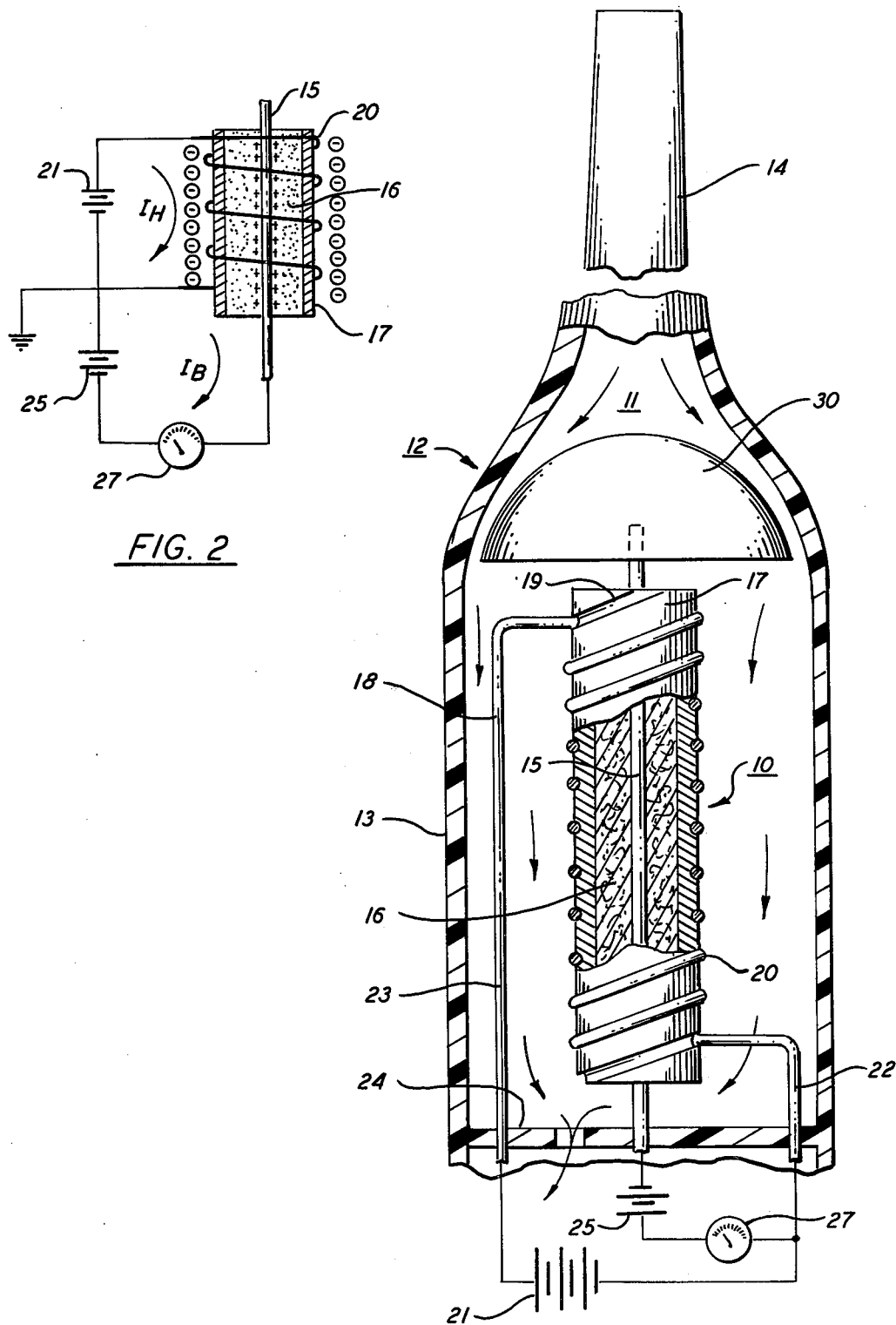

It should be noted at the outset, that the preferred embodiment of the present invention shall be described in reference to a solid state sensor that is selectively tuned to detect the presence of a halogen gas contained within the sample atmosphere to the exclusion of other gases or vapors, including water vapor, that are capable of reacting with the sensing element to produce a troublesome interference signal that could block or otherwise mask the signal of primary interest. It should be clear, however, that the invention is not restricted by the disclosure and the invention has a broader application than that herein described.

Referring now to FIG. 1, the present sensing apparatus, which is generally referenced 10, is shown housed within a hand held probe 12. The probe includes a housing 13, which encloses the sensing device 10, and a hollow "sniffer" tube 14 of elongated construction. Although not shown, a suction producing means is further provided that is operatively connected to the probe and which is arranged to draw a relatively low velocity stream of test atmosphere through the sniffer tube past sensing element 16 as depicted by the arrows. In operation, the open end of the sniffer tube is directed into an area containing the subject atmosphere to be tested and a sample of the atmosphere pulled into the housing with a minimum amount of turbulence where it is allowed to quietly blanket the sensor.

Sensing device 10, which is contained within housing 13, includes a cylindrical solid state sensing element 16 that is contained within a shield 17 of substantially cylindrical form. An elongated electrode 15 is coaxially aligned within the sensing element and extends outwardly from the element beyond the two end faces of the shield. The upper extended end of the electrode, as viewed in FIG. 1, is arranged to support a semicircular flow deflector 30 within entrance region 11 through which the sniffer tube 14 discharges a sample flow into the housing 13. The outer surface of the deflector is contoured to generally complement the interior wall of the housing within the entrance region to establish an annular entrance into the housing through which a test sample is admitted. The deflector, in operation, protects the thermally sensitive components of the sensing apparatus from direct impingement by the incoming flow stream thereby insuring that the operating temperature of the detecting system remains relatively stable during the test period. As will be explained in greater detail below, the ability to maintain stable conditions at the surface of the sensing device plays an important role in the ability of the present device to selectively discern the presence of one reactive gas or vapor in the presence of one or more other reactive constituents.

The opposite or lower extended end of the electrode is passed through the transversely extended bottom wall 24 of the housing and is secured by any suitable means therein to support the electrode and thus the sensing element assembly, in axial alignment within the housing. The lower end of the electrode, that passes downwardly through the wall, is electrically connected to the negative side of a biasing battery 25, the function of which will be explained below.

A heating coil 20, formed of a single piece of platinum wire, is spirally would about the outer surface of shield 17. In assembly, the turns of the coil are securely seated within a helical groove 19 formed in the shield to provide for a uniform spacing between turns. The terminal ends 22, 23 of the coil are turned downwardly and brought through the bottom wall 24 of the housing. The ends of the coil are connected over a D.C. power supply in the form of battery 21 which provides power by which the coil is energized. The temperature produced at the outer surface of the shield is a function, among other things, of the number of turns per inch of the coil and the power output of the battery. As can be seen by varying one or both of these parameters, the operating temperature at the surface of the sensing device can be conveniently controlled.

An electrical detecting circuit made up of previously noted biasing battery 25 and ammeter 27 is connected between the lower terminal 22 of the heating coil, which represents electrical ground in the electrical system, and the electrode 15. A biasing potential is thus placed over the heater coil and the electrode. The shield is formed of a selected material that will prevent current from flowing in the circuit until such time as an electron flow is established through the shield.

Preferably, in the illustrated embodiment of the invention, the solid state sensing element 16 is formed of a metal salt, generally selected from a class of materials including sodium silicate and lithium silicate which contain alkali metal ions. The solid state sensing element 16 is fabricated by first placing an anhydrous salt of the selected material in a crucible and heating the material to about 1200° C. for thirty minutes. The material is removed from the crucible and allowed to cool at room temperature. Upon cooling, the material, which is now in a hard ceramic form, is ground to a fine powder in a grinding jar, ballmill, or the like. Next, elongated wire electrode 15 is supported in axial alignment within the shield 17 and the prepared powder tamped into the cylinder so that it contacts both the inner wall of the cylinder and the outer wall of the electrode to completely fill the void therebetween. Sufficient pressure is applied to the powder to produce a high strength mechanical bond between the adjacent particles and the surrounding components thus providing for a relatively unitized homogeneous three element structure.

The shield 17 is preferably formed of aluminum oxide which is substantially devoid of alkali metal ions and which exhibits good operating characteristics at elevated temperatures. In practice, helical groove 19 can be formed in the outer wall of the shield by any suitable forming or machining operation to a depth sufficient to securely support the heating coil in assembly to prevent unwanted slippage thereof and further strengthen the assembly.

In operation, the shield 17 functions as an electrical barrier in the biasing network to block the flow of current between the heating coil wire and the electrode at ambient temperatures. Accordingly, the electrode is held by the biasing battery at a relatively high negative potential, that is, a potential below the ground potential maintained at terminal 22. Accordingly, positive ions contained in sensing element 16 are drawn or otherwise attracted toward the electrode and become aligned therewith within the central core of the element. This condition is schematically depicted in FIG. 2. Negative ions that might be present in the atmosphere adjacent the shield are prevented from moving across the depletion boundary and thus remain outside the shield. As can be seen, reverse biasing of the electrode tends to hold the positive and negative ions on opposite sides of the shield in an electrically balanced condition. This equilibrium is maintained until some unbalancing force is introduced into the system.

By energizing the heated coil the outer surface of the shield is heated to a desired temperature within a predetermined range wherein a gas or vapor of a given constituent of primary interest is ionized. Heating the shield also causes it to act as an ion control screen to selectively pass ions of the given gas or vapor of interest while effectively preventing the element from reacting with other constituents which may be present in the surrounding atmosphere. As a result, a great deal of the troublesome interference that has heretofore been encountered in this type of solid state sensing device is eliminated to provide for a more reliable and dependable piece of equipment that can be effectively utilized in a broader range of applications.

By way of example, the present device is ideally well suited for detecting the presence of halogen gases in an air atmosphere also containing water vapor. In this application, the heating coil is formed of platinum wire which acts as a catalyst in the halogen ionization process to speed up the reaction and provide for lower operating temperatures. The surface temperature, in this case, is brought to a stable temperature somewhere within a range of between 750° C. and 850° C. To achieve this desired operating temperature a 0.006 inch diameter heater wire wound to between 30 and 40 turns per inch is employed which is energized using a 5 volt source of D.C. power. The electrode is biased to a negative 3.65 volts using a battery connected in the circuitry as described above while the wall thickness of the aluminum oxide shield is maintained at between 0.09 and 0.10 inches. Under these conditions it has been found that the presence of a halogen gas can be accurately detected in an atmosphere containing water vapor that is brought into operative communication with the presence sensor without producing interference signals which have heretofore caused a great deal of difficulty in this particular application.

As can be seen, the sensor of the present invention, because of its simplicity, can be conveniently constructed with very little expense on a mass production basis. The device is compact, light and portable and, because of its selectivity, ideally suited for detecting the presence of halogen gases in a wide range of applications.

While this invention has been described with reference to the structure disclosed herein, it is not confined to the specific details as set forth and the application is intended to cover such modifications or changes as may come within the scope of the following claims.

I claim:

1. The method of forming a solid state sensing device for detecting the presence of given gases and vapors in an atmosphere including providing a hollow ion shield formed of a material that is deplete in alkali metal ions, centering an elongated electrode along the axis of the shield, packing a granulated reactive material of an alkali metal compound into the shield under sufficient pressure to hold the material tightly between the electrode and the inner wall of the shield.

2. The method of claim 1 that further includes the step of winding a heating coil about the outside of the shield.

3. The method of claim 2 that further includes the step of forming a spiral groove in the outer surface of the shield for receiving the heater coil therein.

4. The method of claim 3 that further includes the step of connecting a biasing means between the heating coil and the electrode for applying a voltage over the gap therebetween.

5. The method of claim 1 wherein the shield is formed of aluminum oxide ($Al_2O_3$).

6. The method of claim 5 wherein the reactive material is a salt of an alkali metal.

* * * * *